(12) United States Patent
Le et al.

(10) Patent No.: US 9,187,355 B2
(45) Date of Patent: Nov. 17, 2015

(54) PRODUCTION OF VOLATILE FATTY ACIDS BY MEANS OF MESOPHILIC FERMENTATION OF SLUDGE

(75) Inventors: Minh Son Le, Northwich (GB); Ruyi Hu, Chester (GB); Sean Tyrrel, Ampthill (GB)

(73) Assignee: United Utilities PLC, Great Sankey (GB)

( * ) Notice: Subject to any disclaimer, the term of this patent is extended or adjusted under 35 U.S.C. 154(b) by 650 days.

(21) Appl. No.: 12/746,380

(22) PCT Filed: Nov. 28, 2008

(86) PCT No.: PCT/GB2008/003978
§ 371 (c)(1),
(2), (4) Date: Aug. 18, 2010

(87) PCT Pub. No.: WO2009/071878
PCT Pub. Date: Jun. 11, 2009

(65) Prior Publication Data
US 2010/0317089 A1    Dec. 16, 2010

(30) Foreign Application Priority Data
Dec. 6, 2007  (GB) .................................. 0723854.6

(51) Int. Cl.
C12M 1/00       (2006.01)
C12M 3/00       (2006.01)
C02F 11/04      (2006.01)
C02F 3/12       (2006.01)
(Continued)

(52) U.S. Cl.
CPC ............... *C02F 11/04* (2013.01); *C02F 3/1263* (2013.01); *C12M 21/04* (2013.01); *C12M 41/18* (2013.01); *C12M 47/02* (2013.01); *C02F 11/12* (2013.01); *C02F 2209/02* (2013.01); *Y02E 50/343* (2013.01); *Y02W 10/15* (2015.05)

(58) Field of Classification Search
CPC ....... C12M 21/04; C12M 47/02; C12M 47/10
See application file for complete search history.

(56) References Cited

U.S. PATENT DOCUMENTS

| 4,134,830 A | 1/1979 | Skogman et al. |
| 4,735,724 A | 4/1988 | Chynoweth et al. |

(Continued)

FOREIGN PATENT DOCUMENTS

| DE | 3341691 A1 | 5/1985 |
| JP | 2002/361293 A | 12/2002 |

(Continued)

OTHER PUBLICATIONS

United Utilities Plc., "International Search Report" dated Apr. 22, 2009, issued in PCT/GB20081003978, 4 p.

(Continued)

*Primary Examiner* — Nathan Bowers
(74) *Attorney, Agent, or Firm* — Rodney B. Carroll; Conley Rose, P.C.

(57) ABSTRACT

A method and related apparatus for the removal of excess water from sludge, the method comprising the steps of: (1) fermenting the sludge at a temperature in the mesophilic temperature range, (2) maintaining the fermenting sludge for a predetermined period under a hydraulically quiescent condition to achieve phase separation, (3) separately removing the solid phase and liquid phase and (4) feeding the solid phase to the digester for conversion to biogas.

8 Claims, 2 Drawing Sheets

Figure 1:
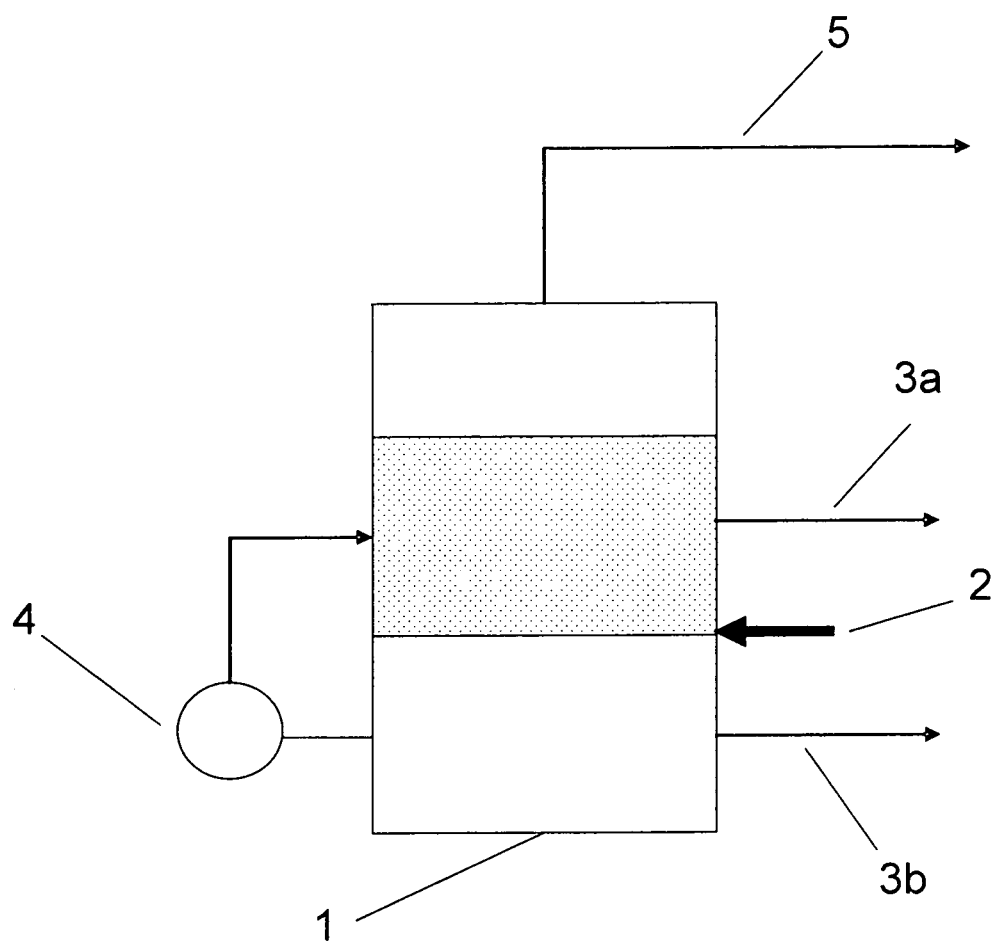

(51) Int. Cl.
*C12M 1/107* (2006.01)
*C12M 1/02* (2006.01)
*C02F 11/12* (2006.01)

(56) References Cited

U.S. PATENT DOCUMENTS

| | | | |
|---|---|---|---|
| 5,185,079 A | 2/1993 | Dague | |
| 5,773,526 A | 6/1998 | Van Dijk et al. | |
| 5,853,589 A | 12/1998 | Desjardins et al. | |
| 6,015,496 A | 1/2000 | Khudenko | |
| 6,368,849 B1 * | 4/2002 | Norddahl | 435/262 |
| 6,569,332 B2 * | 5/2003 | Ainsworth et al. | 210/603 |
| 2002/0102673 A1 * | 8/2002 | Zhang et al. | 435/167 |

FOREIGN PATENT DOCUMENTS

| | | |
|---|---|---|
| JP | 2006/107943 A | 4/2006 |
| KR | 2007/0056260 A | 6/2007 |
| WO | 92/20628 | 11/1992 |
| WO | 2007/083456 A | 7/2007 |

OTHER PUBLICATIONS

United Utilities Plc., "International Preliminary Report on Patentability and Written Opinion" dated Jun. 8, 2010, issued in PCT/GB2008/003978, 8 p.
Moser-Engeler et al., "Fermentation of Raw Sludge on an Industrial Scale and Applications for Elutriating its Dissolved Products and Non-Sedimentable Solids," Wat. Res. vol. 33, No. 16, pp. 3503-3511, 1999.
Rossle et al., "A Review of Characterization Requirements for In-Line Prefermenters. Paper 2: Process Characterization," Water SA, vol. 27, No. 3, Jul. 2001.
Llabres et al., "The Use of Organic Fraction of Municipal Solid Waste Hydrolysis Products for Biological Nutrient Removal in Wastewater Treatment Plants," Wat. Res. vol. 33, No. 1, pp. 214-222, 1999.
Elefsiniotis et al., "Use of Volatile Fatty Acids from an Acid-Phase Digester for Denitrification," Journal of Biotechnology, 114 (2004) pp. 289-297.
Bischof et al., "Abwassertechnik," 1998, XP002521562, pp. 580-591.

* cited by examiner

PRODUCTION OF VOLATILE FATTY ACIDS BY MEANS OF MESOPHILIC FERMENTATION OF SLUDGE

CROSS-REFERENCE TO RELATED APPLICATIONS

This application is a national phase entry of prior PCT Application No. PCT/GB2008/003978 filed 28 Nov. 2008 and entitled "Production of Volatile Fatty Acids by Means of Mesophilic Fermentation of Sludge", hereby incorporated herein by reference, which claims the benefit of GB Patent Application No. 0723854.6 filed 6 Dec. 2007 and entitled "Production of Volatile Fatty Acids by Means of Mesophilic Fermentation of Sludge", hereby incorporated herein by reference.

STATEMENT REGARDING FEDERALLY SPONSORED RESEARCH OR DEVELOPMENT

Not applicable.

The present invention relates to a method suitable for the removal of excess water from sludge containing organic matter of a particulate nature, particularly as a means for increasing the solid residence time in digesters.

In an anaerobic digestion process the organic substrate is biologically converted to a biogas that may be used for power generation. The process is attractive for the treatment of waste products. Such a process is well known in the art and may have many variations. An example of such a process has been described by Ghosh, et al. (1977); and another one described by Dague, et al. (1998). In general, anaerobic digestion comprises a series of complex biochemical reactions mediated by consortia of micro-organisms that convert organic compounds to methane and carbon dioxide. It is a stabilization process achieving odour, pathogen, and mass reduction. During the process, particulates are solubilised and large polymers are converted to monomers. Subsequently, the monomers are fermented to simple substances and finally to a biogas. According to Bach (1943), the total digestion time for sewage sludge should be approximately 15 days. Bach (1943) also suggested that some components of the sludge required considerable time and energy to be mineralised. It is a known fact that the digestion of particulate matter requires longer periods of time than soluble matter. In the digestion of sewage sludge, which contains a high proportion of particulate matter, a treatment period of 15 days typically produces only 40% reduction in the organic content of the sludge.

It is desirable to maximise the reduction of the organic content of the sludge to achieve maximum biogas conversion. It is known that a reduction of the organic content of the sludge may be increased by increasing the solid residence time in the digester. Traditionally, this has been achieved by reducing the volumetric feeding rate to the digester while maintaining the same solid loading rate to the digester. Wright (1978) described a sludge thickening method and apparatus that may be used for this purpose. The Wright invention included a conventional settling vessel with moving rake and pickets. However, the Wright method was found to be unreliable and unfortunately did not achieve any significant commercial success. Further developments to try and improve the effectiveness of the above thickening process were undertaken by Kormanik, et al. (1986). This Kormanik invention, which is known as the gravity belt thickener, involves the use of a water-permeable belt and the addition of a polymer to flocculate to the sludge in order to effect water removal.

The gravity belt thickener has been a successful invention and its application has been widespread. Typically, the gravity belt thickener is capable of raising the solid content of sewage sludge from 3% weight/volume (w/v) to 6% weight/volume (w/v) before the sludge is fed to the digester. Effectively, the gravity belt thickener is capable of increasing the solid residence time in the digester by 100%. However, it is necessary to house such expensive equipment in high cost buildings. Furthermore, the use of a polymer in the process significantly modifies the sludge rheology making it very difficult to pump and mix.

Another method of removing water from sludge has been offered by Agranonik, et al. (1998) which involves saturating water in the system with air. The Agranonik method was intended for use with an activated sludge process. However, since the final solid content of the sludge in the system remained below 3% weight/volume (w/v), it is not suitable for use in a digestion process.

It is clear from the foregoing that while it is desirable to remove excess water from sludge that is to be digested in order to increase the retention time of the organic solid particles in the digester, there are no known methods that can achieve this goal without some drawbacks.

It is therefore an aim of the present invention to provide a method for the removal of excess water from sludge, particularly before digestion or even during the digestion process of sewage sludge and the like. Such a method would overcome the disadvantages of methods described prior hereto.

It is a further aim of the present invention is to provide an apparatus for the removal of excess water from sludge, particularly before digestion or even during the digestion process of sewage sludge and the like. Such an apparatus is simple to construct and can be integrated easily and readily to existing digestion assets.

Yet another aim of the present invention is to provide a volatile fatty acid rich liquor stream useful as a carbon source for biological nutrient removal applications.

Therefore, according to a first aspect of the present invention there is provided a method suitable for the removal of excess water from sludge, the method comprising the steps of:

(i) fermenting the sludge at a temperature in the mesophilic temperature range;

(ii) maintaining the fermenting sludge for a predetermined period under a hydraulically quiescent condition to achieve phase separation; and (iii) separately removing the solid phase and liquid phase.

The method preferably further comprises the step of feeding the solid phase to the digester for conversion to biogas In the method according to the first aspect of the present invention the sludge is preferably fermented at a temperature in the range of 15° C. to 45° C., more preferably the sludge is fermented at a temperature in the range of 30° C. to 42° C.

In addition, in the method according to the first aspect of the present invention the fermenting sludge is preferably maintained under a hydraulically quiescent condition for a period of between 12 hours to 120 hours, more preferably, the fermenting sludge is maintained under a hydraulically quiescent condition for a period of between 16 hours to 48 hours.

Furthermore, the phase separation of the method is assisted by nascent biogas bubbles, and the sludge preferably comprises raw sludge.

In accordance with the method according to the first aspect of the present invention, the sludge preferably comprises an initial solid concentration of between 1% to 5% weight/volume (w/v), more preferably, the solid phase comprises a solid concentration of between 5% to 12% weight/volume (w/v).

Most preferably the solid phase comprises a solid concentration of between 5.5% to 10% weight/volume (w/v).

Also in accordance with the method according to the first aspect of the present invention, the liquid phase comprises a solid concentration less than 0.5% weight/volume (w/v). More preferably the liquid phase comprises a solid concentration less than 0.35% weight/volume (w/v).

According to a second aspect of the present invention there is provided an apparatus suitable for the removal of excess water from sludge in the method outlined above, the apparatus comprising:

a fermentation vessel;
means to provide mixing and for maintaining the temperature in the fermentation vessel within the mesophilic range,
means for delivering raw sludge to the fermentation vessel,
means for removing the solid phase from the fermentation vessel, and
means for removing liquid phase from the fermentation vessel.

The apparatus preferably further comprises a means for removing biogas from the fermentation vessel. The means to provide mixing and for maintaining the temperature in the fermentation vessel preferably comprises a separate heating device and a separate mixing device. The means for removing the solid phase and the means for removing liquid phase may be combined into a single unit.

Finally according to a third aspect of the present invention there is provided a volatile fatty acid rich liquor stream suitable for use as a carbon source for biological nutrient removal applications, the stream being derived from the liquid phase when using the method according to the first aspect of the present invention or the apparatus according to the second aspect of the present invention.

It will be understood that the term "raw" sludge is used to refer to a sludge that has a relatively high organic content and does not exclude the possibility that there has been some degree of pre-treatment on the sludge. Raw sludge typically contains 65 to 85% weight/weight (w/w) organic components whilst the remainder comprises inorganic components. It should be noted that the term "fermentation" refers to a biological conversion process that may also include digestion.

During the early stages of sludge fermentation the substrate undergoes hydrolysis and acidogenesis. These processes result in the evolution of a small quantity of biogas that typically comprises over 80% carbon dioxide. Surprisingly, the nascent biogas bubbles have the ability to attach themselves to the raw sludge particles and cause the latter to float. Left undisturbed, in other words under a hydraulically quiescent condition, the essentially raw sludge separates into a top layer of concentrated sludge and a bottom layer of sludge liquor. The present inventors believe, whilst not wishing to be bound by any particular theory, that the surface of raw sludge particles possess a degree of hydrophobicity, therefore the raw sludge particles have a tendency to attract gas bubbles which are naturally hydrophobic. On the other hand, under the effect of digestion sludge particles gradually lose their hydrophobicity and the tendency to attract gas bubbles. Digested sludge particles, being denser than water tend to settle towards the bottom layer of sludge liquor.

The splitting of a sludge stream into layers of similar materials is known as phase separation. A top layer of concentrated sludge is often referred to as the solid phase and a bottom layer of sludge liquor is often referred as the liquid phase. In order to make good industrial use of phase separation, the present inventors have carried a study of the process conditions and parameters that affect the process kinetics of such phase separation.

Phase separation is essentially a side effect of a fermentation processes and is significantly affected by the process temperature. Separation can be achieved within the temperature range of 15° C. to 45° C. At the extremes of this temperature range the bacterial activity become too sluggish for the process to be useful. As the temperature increases the viscosity of the medium is reduced leading to an increase in the rate of separation. The optimum process temperature for the separation is to be found in the range of 30° C. to 42° C.

As mentioned above, raw sludge particles and digested sludge particles appear to behave differently towards nascent biogas bubbles. Sludge that has been digested for more than 12 days appears to have little affinity for the nascent biogas bubbles. In a phase separation system where the sludge is a mixture of raw sludge and digested sludge, the process may result in three distinct layers, with the liquid phase in the middle and the solid phase layer of raw sludge and digested sludge layer at the top and bottom of the system respectively. The initial concentration of solid in the sludge has a significant influence on the rate of separation but not the final solid concentration in the separated phases. Generally, a higher initial solid concentration results in a more sluggish separation. Sludge streams with initial solid concentration of 1% to 5% weight/volume (w/v) are suitable for use with this invention. The final solid concentrations in all the separated phases have been found to be within a very narrow range of values. The solid phase typically comprises a solid content of 6% to 12% weight/volume (w/v); and the liquid phase typically comprises a solid content of about 0.3% weight/volume (w/v).

In order to initiate the phase separation process, the sludge normally has to be heated up to a sufficient working temperature. Heating can be achieved by any convenient means, for example but not limited to, injecting steam directly into the sludge or by recirculating the cold sludge through a heat exchanger which has a hot water supply. Sludge normally contains a wide range of suitable bacteria which are capable of commencing the process of fermentation and produce the necessary biogas as soon as the temperature of the system reaches a workable range. To ensure uniform fermentation and gas production, it is desirable to mix the sludge thoroughly during the heating period. Mixing may be terminated as soon as the sludge reaches the desired working temperature. Phase separation commences as soon as the fermenting sludge is left in a quiescent state. As the process proceeds the solid phase layer and the bottom layer (if digested sludge is involved) increase both in volume and in solid concentration. At the same time, a liquid phase that gradually becomes depleted of solid particles appears. Any phase separation activity normally ceases after a quiescent period. A period of 12 hours to 36 hours is normally required to complete the separation, but periods of up to 6 days may also be used although longer periods are obviously less convenient.

A quiescent state means that the sludge is left undisturbed, since any disturbance would impede the phase separation process. Nevertheless, as separation only takes place along the gravitational axis, in other words only in the vertical plane, some radial movements are therefore permissible. For instance, the whole sludge mass may be rotated about the vertical axis without any detrimental effect on the phase separation. Radial movements may be beneficial as they tend to cause the solid phase to migrate toward the centre of the fermentation vessel and would facilitate its subsequent removal.

The liquid phase resulting from the phase separation process normally contains all the dissolved substances including ammonia, volatile fatty acids, etc. Such a liquid phase stream provides a valuable carbon source for biological nutrient removal applications. Biological nutrient removal processes are well known in the water industry and the use of volatile fatty acids for enhanced biological phosphorus removal, for example, is well established.

Figure 2:
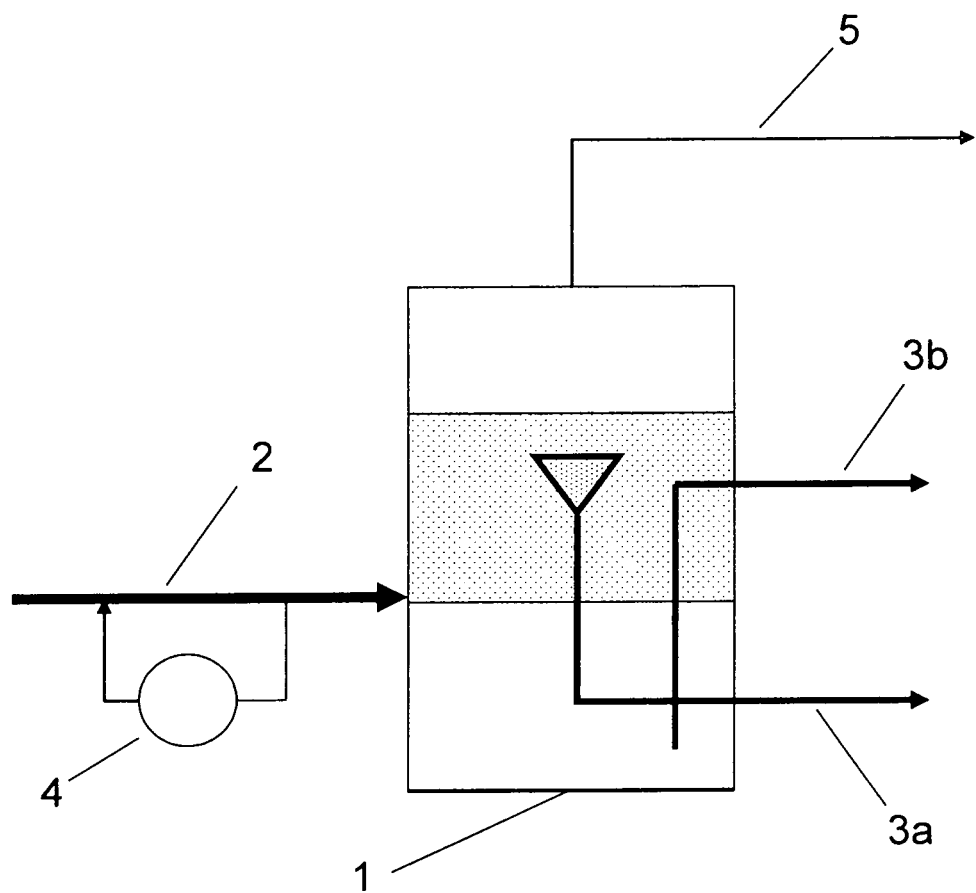

For a better understanding of the present invention and to show more clearly how it may be carried into effect, the invention will now be described in further details with reference to and by way of example only, to the accompanying examples and drawings in which:

FIG. 1—is a diagrammatic sketch of an apparatus according, to the first embodiment of the present invention; and FIG. 2—is a diagrammatic sketch of an apparatus according to the second embodiment of the present invention.

Referring to FIG. 1 of the accompanying drawings, an apparatus for the removal of excess water from sludge according to one embodiment of the present invention is illustrated. The apparatus comprises a fermentation vessel (1) for fermentation and phase separation of the sludge, means (2) for delivering raw sludge to the fermentation vessel, means for removing the solid phase (3a), means for removing the liquid phase (3b), means to provide mixing and for maintaining the temperature (4) in the fermentation vessel, and means for removing any biogas (5) from the fermentation vessel. Such a device is ideally suited for batch operations.

Referring to FIG. 2 of the accompanying drawings, an apparatus for the removal of excess water from sludge according to a second embodiment of the present invention is illustrated. The apparatus comprises a fermentation vessel (1) for fermentation and phase separation of the sludge, means for delivering raw sludge (2) to the fermentation vessel, means for removing the solid phase (3a), means for removing the liquid phase (3b), means to provide mixing and for maintaining the temperature (4) in the fermentation vessel, and means for removing any biogas (5) from the fermentation vessel. In this embodiment the means for removing the solid phase (3a) includes a bell-mouth shaped inlet to facilitate the sludge flow. Such a device is more ideally suited for continuous process operations.

The fermentation vessel (1) for fermentation and phase separation may be of any suitable configuration. Tanks of circular cross section with a minimum height to diameter ratio of 1.0 are to be preferred.

Sludge may be delivered to the fermentation vessel (1) by any convenient means, for example by pumping. Suitable pump types include centrifugal pumps, progressive cavity pumps and helical screw pumps. The latter is the most preferable means for delivering raw sludge (2) to the fermentation vessel.

The solid phase and liquid phase may be removed from the fermentation vessel (1) by any convenient means, for example by pumping. Suitable pump types include centrifugal pumps, progressive cavity pumps and helical screw pumps. Gas lift is a preferable means for removing the solid phase (3a) from the fermentation vessel. Gravity drainage is a preferable means for removing the liquid phase (3b) from the fermentation vessel.

The means for mixing and temperature maintenance (4) can often be combined into a single unit as illustrated by the present drawings. It is possible to have separate mixing and temperature maintenance units depending on the operator preference. It is also possible to carry out the heating and mixing operation as a pre-treatment before the sludge is delivered to the fermentation vessel (1) in which case it does not require further heating and mixing as illustrated by FIG. 2. In all cases, the fermentation vessel (1) is preferably lagged to minimise any heat loss.

For continuous process operation it is more convenient to carry out the heating and mixing operation as a pre-treatment. Also, for continuous operation the solid phase and liquid phase would be removed simultaneously, therefore, ideally the raw sludge is preferably delivered and distributed into a region of the fermentation vessel that ensures minimum disturbance to the solid phase and liquid phase layers. For a batch operation the means for removing the solid phase (3a), and the means for removing the liquid phase (3b) may be combined as a single unit. Such a unit is ideally placed at the lowest point in the fermentation vessel (1) so that the different phases may be removed one after another.

Phase separation is preferably carried out under anaerobic conditions so that any biogas is conveniently collected and treated to avoid odour nuisance. A simple treatment is blending and use in a combustion process with biogas from a digester.

The present invention will now be explained further by way of the following examples.

EXAMPLE 1

Un-thickened sludge samples with different initial sludge solid concentrations were taken from a sewage treatment works (site A). Two samples each of 800 mL volume were fermented in two separate fermentation vessels at 42° C. without mixing for 48 hours. The results of the phase separation are as shown by Table 1. The results suggest that sludge with low initial solid concentration separates more rapidly then sludge with higher solid concentration.

TABLE 1

Variation of phase separation rates with time and initial sludge solid concentration.

| | Parameters | |
| --- | --- | --- |
| Quiescent period (hours) | Sample A1 Liquid phase volume (mL) | Sample A2 Liquid phase Volume (mL) |
| 0 | 0 | 0 |
| 2 | 250 | 0 |
| 5 | 450 | 100 |
| 21 | 600 | 400 |
| 25 | 650 | 410 |
| 29 | 650 | 420 |
| 45 | 650 | 460 |
| Initial sludge solid concentration, % w/v | 2.4 | 4.1 |
| Liquid phase final solid concentration, % w/v | 0.2 | 0.3 |
| Solid phase final solid concentration, % w/v | 8.6 | 9.8 |

EXAMPLE 2

The experiments in Example 1 were repeated using sludge samples from a number of different sewage works. The results as shown in Table 2 suggest that the final solid concentrations in all the separated phases fall within a very narrow range of values. The concentration factor or the ratio of the solid phase final concentration to the initial sludge concentration was in the range 2 times to 3.5 times.

TABLE 2

Variations of phase separation characteristics by sludge samples from different sewage works.

| Sludge sources | Initial sludge | liquid phase | solid phase | Concentration factor |
|---|---|---|---|---|
| Site A | 2.40% | 0.20% | 8.60% | 3.58 times |
| Site C | 2.90% | 0.20% | 5.80% | 2.00 times |
| Site D | 3.50% | 0.30% | 8.80% | 2.51 times |
| Site A | 4.10% | 0.30% | 9.80% | 2.39 times |
| Site D | 4.30% | 0.40% | 10.10% | 2.35 times |
| Site B | 4.90% | 0.40% | 10.40% | 2.12 times |

EXAMPLE 3

A 40 liter sample of un-thickened sludge from a sewage treatment works (site C) was divided into two sub-samples each of 20 liters in volume. Both sub-samples were fermented in separate fermentation vessels at different temperature and without mixing for 96 hours. The results of the phase separation were as shown by Table 3. The results clearly indicated that the higher temperature produced a much superior phase separation both in terms of higher rate and higher solid phase final solid concentration.

TABLE 3

Variations of phase separation rates with time and temperature.

| Quiescent period (hours) | Parameters | |
|---|---|---|
| | Sample C1 at 15° C. Liquid phase volume (L) | Sample C2 at 42° C. Liquid phase volume (L) |
| 0 | 0 | 0 |
| 16 | 7.37 | 11.43 |
| 24 | 7.89 | 12.86 |
| 40 | 11.05 | 13.81 |
| 48 | 12.11 | 14.00 |
| 64 | 12.20 | 14.00 |
| 72 | 12.63 | 14.29 |
| 88 | 13.00 | 14.29 |
| 96 | 13.68 | 14.29 |
| Initial sludge solid concentration, % w/v | 2.9 | 2.9 |
| Liquid phase final solid concentration, % w/v | 0.3 | 0.3 |
| Solid phase final solid concentration, % w/v | 7.1 | 7.9 |

EXAMPLE 4

Sludge from site B was fermented and dewatered by phase separation over a period of 48 hours at 42° C. The solid phase was digested for 14 days at 35° C. Various analytical determinations were carried out on the sample before and after the phase separation experiment and after digestion. The results of the determinations were as shown by Table 4.

TABLE 4

Analysis of site B sludge before and after phase separation at 42° C. and after digestion.

| | Initial sludge | liquid phase | solid phase | After digestion |
|---|---|---|---|---|
| DS % w/v | 4.35 | 0.40 | 10.10 | 5.94 |
| VS % w/w | 71.84 | 71 | 69.48 | 57.90 |
| Total COD, mg/L | 54,864 | 15,347 | 127,284 | 62,990 |
| Soluble COD, mg/L | 5,891 | 10,502 | 10,300 | 4,942 |
| PH | 5.92 | 5.90 | 5.97 | 7.32 |
| Alkalinity, mg/L | 1,365 | 2,450 | 2,540 | 5,350 |
| Ammonia, mg/L | 210 | 605 | 650 | 1,470 |
| Volatile Fatty Acids, mg/L | 1,625 | 3,850 | 3,800 | 262 |
| E. coli, MPN/g solid | 4,060,000 | 8,288 | 10,770 | 3,943 |

EXAMPLE 5

An apparatus for the removal of excess water from sludge was constructed. The vessel for fermentation and phase separation of the sludge was made of glass reinforced plastic and was insulated. The vessel had a working volume of 4,000 liters. A single outlet pipe with a valve at the bottom of the vessel was employed as a means for removing the solid phase and the liquid phase at the end of the phase separation process. A recirculation pump was used as the means for mixing. An electrical element was used as a heating means and for maintaining the temperature the fermentation vessel at 42° C. A batch of sludge of 4,000 liters was fermented and the results were as shown by Table 5.

TABLE 5

Results of the phase separation trial with the large scale apparatus.

| Parameters | Initial sludge | liquid phase | solid phase |
|---|---|---|---|
| Solid concentration, % w/v | 3.50% | 0.30% | 8.80% |
| Volume, L | 4,000 | 2,490 | 1,510 |

It will be appreciated that many modifications and enhancements may be made to the basic method and apparatus outlined herein. For instance, the solid phase may be re-suspended in a wastewater and further fermented in order to extract more volatile fatty acid from the solid phase. Phase separation may be carried out in a number of vessels in series, etc.

Other possible modifications or applications will be readily apparent to the appropriately skilled person.

REFERENCES

U.S. Pat. No. 2,315,577 (Bach, 1943)
U.S. Pat. No. 4,022,665 (Ghosh, et al., 1977)
U.S. Pat. No. 5,746,919 (Dague, et al., 1998)
U.S. Pat. No. 4,120,791 (Wright, 1978)
U.S. Pat. No. 4,595,499 (Kormanik, et al., 1986)
U.S. Pat. No. 5,849,191 (Agranonik, et al. 1998)

The invention claimed is:
1. A method of removing excess water from raw sludge to produce concentrated sludge particles and a volatile fatty acid rich liquor stream comprising the steps of:
(i) introducing the raw sludge with an initial solids concentration of between 1% and 5% weight/volume (w/v) and from 65 to 85% weight/weight organic matter into a fermentation vessel;

(ii) fermenting the sludge under essentially anaerobic conditions at a temperature in the range of 30° C. to 42° C. using only indigenous bacteria present in the sludge to generate nascent biogas bubbles comprising greater than 80% carbon dioxide said fermenting being substantially completed in a period of between 12 hours and 120 hours under a substantially hydraulically quiescent condition leaving the sludge undisturbed to allow said bubbles to effect flotation of sludge particles present in the fermenting sludge to form a concentrated surface layer of said particles and in which said particles in said concentrated surface layer are digested and sink to the bottom of the vessel to form a layer of digested sludge thereby achieving a phase separation of the sludge during this period into three layers comprising:
  a) a first solid phase surface layer of concentrated sludge particles;
  b) a second liquid phase middle layer of sludge liquor substantially depleted of the solid particles; and
  c) a third digested sludge bottom layer at the bottom of the vessel;
(iii) separately removing the solid phase layer and liquid phase layer; and
(iv) deriving a volatile fatty acid liquor stream from the liquid phase layer.

2. A method according to claim 1, further comprising the step of feeding the solid phase to the digester for conversion to biogas.

3. A method according to claim 1, wherein the fermenting sludge is maintained under a hydraulically quiescent condition for a period of between 16 hours to 48 hours.

4. A method according to claim 1, wherein the solid phase comprises a solid concentration of between 5% to 12% weight/volume (w/v).

5. A method according to claim 4, wherein the solid phase comprises a solid concentration of between 5.5% to 10% weight/volume (w/v).

6. A method according to claim 1, wherein the liquid phase comprises a solid concentration less than 0.5% weight/volume (w/v).

7. A method according to claim 6, wherein the liquid phase comprises a solid concentration less than 0.35% weight/volume (w/v).

8. A method according to claim 1 further comprising the step of:
  v) removing biogas generated during the fermentation stage from the fermentation vessel.

* * * * *